United States Patent
Powers

(10) Patent No.: US 9,233,255 B2
(45) Date of Patent: Jan. 12, 2016

(54) SYSTEM AND METHOD FOR PROVIDING EVENT SUMMARY INFORMATION USING AN ENCODED ECG WAVEFORM

(75) Inventor: Daniel Powers, Seattle, WA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 1895 days.

(21) Appl. No.: 12/067,213

(22) PCT Filed: Sep. 15, 2006

(86) PCT No.: PCT/IB2006/053322
§ 371 (c)(1),
(2), (4) Date: Mar. 18, 2008

(87) PCT Pub. No.: WO2007/034394
PCT Pub. Date: Mar. 29, 2007

(65) Prior Publication Data
US 2008/0255625 A1 Oct. 16, 2008

Related U.S. Application Data

(60) Provisional application No. 60/719,634, filed on Sep. 22, 2005.

(51) Int. Cl.
*A61N 1/39* (2006.01)
*A61B 5/00* (2006.01)
*A61B 5/0402* (2006.01)
*A61B 5/0432* (2006.01)

(52) U.S. Cl.
CPC .............. *A61N 1/39* (2013.01); *A61B 5/0006* (2013.01); *A61N 1/3968* (2013.01); *A61B 5/04021* (2013.01); *A61B 5/04325* (2013.01); *A61B 2562/227* (2013.01); *A61N 1/3993* (2013.01)

(58) Field of Classification Search
CPC ..... A61N 1/39; A61N 1/3993; A61N 1/3968; A61B 5/0006; A61B 5/04325; A61B 5/04021
USPC ............................................................ 607/5
See application file for complete search history.

(56) References Cited

U.S. PATENT DOCUMENTS

| 4,267,576 A | 5/1981 | Power et al. |
| 4,506,677 A | 3/1985 | Lambert |
| 5,105,821 A | 4/1992 | Reyes |
| 5,549,115 A | 8/1996 | Morgan et al. |
| 5,680,864 A | 10/1997 | Morgan et al. |

(Continued)

FOREIGN PATENT DOCUMENTS

| EP | 0409591 A1 | 1/1991 |
| GB | 9617653 A1 | 6/1996 |

(Continued)

OTHER PUBLICATIONS

Cummins et al: Improving Survival From Sudden Cardiac Arrest: The "Chain of Survival" Concept:; Circulation, vol. 83, May 1991, pp. 1832-1847.

*Primary Examiner* — Eric D. Bertram

(57) ABSTRACT

Systems and methods for transferring medical information from a first medical monitoring device to a second device are provided. Medical information from the first medical monitoring device is encoded as an ECG waveform and the ECG waveform having the encoded medical information is provided to the second device as an input ECG waveform.

1 Claim, 6 Drawing Sheets

(56) References Cited

U.S. PATENT DOCUMENTS

| | | | |
|---|---|---|---|
| 5,716,380 A * | 2/1998 | Yerkovich et al. | 607/5 |
| 5,785,043 A | 7/1998 | Cyrus et al. | |
| 5,899,866 A | 5/1999 | Cyrus et al. | |
| 5,951,485 A | 9/1999 | Cyrus et al. | |
| 5,956,013 A | 9/1999 | Raj et al. | |
| 6,088,617 A | 7/2000 | Arand et al. | |
| 6,141,584 A | 10/2000 | Rockwell et al. | |
| 6,321,113 B1 | 11/2001 | Parker et al. | |
| 6,381,492 B1 | 4/2002 | Rockwell et al. | |
| 6,405,083 B1 | 6/2002 | Rockwell et al. | |
| 6,438,417 B1 | 8/2002 | Rockwell et al. | |
| 6,754,526 B2 | 6/2004 | Daynes et al. | |
| 6,990,371 B2 | 1/2006 | Powers et al. | |
| 2003/0055460 A1 * | 3/2003 | Owen et al. | 607/5 |
| 2003/0069510 A1 * | 4/2003 | Semler | 600/509 |
| 2003/0105404 A1 | 6/2003 | Galen et al. | |
| 2004/0204743 A1 | 10/2004 | McGrath et al. | |
| 2004/0215246 A1 | 10/2004 | Powers et al. | |
| 2004/0215271 A1 | 10/2004 | Sullivan | |
| 2005/0065557 A1 | 3/2005 | Powers et al. | |

FOREIGN PATENT DOCUMENTS

| | | |
|---|---|---|
| GB | 2388323 A | 11/2003 |
| JP | 3155831 A | 7/1991 |
| JP | 2004525698 A | 8/2004 |
| WO | 02074382 A2 | 9/2002 |
| WO | 2004058351 A1 | 7/2004 |

* cited by examiner

SYSTEM AND METHOD FOR PROVIDING EVENT SUMMARY INFORMATION USING AN ENCODED ECG WAVEFORM

This invention relates to medical equipment, and in particular, to the encoding of defibrillator event summary information in the form of an encoded ECG waveform for playback on a second defibrillator.

One frequent consequence of heart disease is the development of cardiac arrest associated with a heart arrhythmia such as ventricular fibrillation. Ventricular fibrillation may be treated by delivering an electrical shock to the patient's heart through the use of a defibrillator. Cardiopulmonary resuscitation ("CPR") is commonly used to maintain life support for victims of cardiac arrest until a defibrillator can be deployed to treat the arrhythmia.

The chances of surviving a cardiac arrest decrease rapidly over the time following the arrest. Quick response to a cardiac arrest by performing CPR and by administering a defibrillating shock is therefore of critical importance. The American Heart Association's "Chain of Survival" recites the following steps:

1. Early access to emergency care, such as by activating an emergency medical system ("EMS");
2. Early CPR initiated by a bystander or other first responder using basic life support ("BLS") techniques to help the patient survive until more advanced care arrives;
3. Early defibrillation; and
4. Early advanced cardiac care. The benefits of this approach are discussed in more detail in Cummins, et al. "Improving Survival From Sudden Cardiac Arrest: the 'Chain of Survival' Concept," 83 Circulation 1832-47 (May 1991).

EMS providers are playing an active role in implementing the Chain of Survival concept. Tiered EMS systems are emerging in many geographical areas and are typically divided between first responders, BLS providers, and advanced cardiac life support ("ACLS") providers. First responders and BLS providers, often called EMT(B) or EMT-basic, the front line personnel who are first to reach a patient, are now being trained and authorized to use automatic external defibrillators ("AEDs") to provide early defibrillation.

AEDs deliver a high-amplitude electrical impulse to the heart in order to allow the resumption of normal rhythm and contractile function in the patients who are experiencing ventricular fibrillation ("VF") or ventricular tachycardia ("VT") that is not accompanied by a palpable pulse. AEDs differ from manual defibrillators in that AEDs can automatically analyze the electrocardiogram ("ECG") rhythm to determine if defibrillation is necessary. In nearly all AED designs, when a shockable rhythm is detected the first responder is prompted to press a shock button to deliver the defibrillation shock to the patient. Paramedic defibrillators often combine the AED and manual functions into one unit to allow for use by personnel with differing levels of training.

AEDs are designed to be used primarily by first responders who may not be trained in ACLS techniques. In the pre-hospital setting, these first responders may include emergency medical technicians trained in defibrillation ("EMT-Ds"), police officers, flight attendants, security personnel, occupational health nurses, and firefighters. AEDs can also be used in areas of the hospital where personnel trained in ACLS are not readily available.

In many EMS systems, the next link in the Chain of Survival is provided with the arrival of ACLS trained paramedics equipped with full featured defibrillators/cardiac monitors ("paramedic defibrillators"). Alternatively, if no ACLS trained personnel are available, the patient is directly transported to a hospital department where ACLS care can be provided. In either case, a handoff of the patient takes place between the first responder and subsequent ACLS personnel.

As part of the handoff process, medical information obtained at the scene of the initial resuscitation effort and stored within the defibrillator must be transferred along with the patient regarding what has taken place during treatment. Commonly referred to as a code summary or an event summary, such information typically may include an ECG strip as well as markers for such events as the time of initial cardiac arrest, initiation of CPR, administration of drugs, delivery of defibrillation shocks, and so on. Such medical information contained in the event summary should be as complete and accurate as possible to ensure continuity of care and to enable the attending physician to provide the most appropriate follow-up care to the patient. It is desirable that the medical information stored in the event summary be transported with the patient during the various handoffs along the Chain of Survival.

The event summary, as previously mentioned, includes a paper ECG strip that is printed by defibrillators having built-in printers. Typically, paramedic defibrillators have built-in printers that are used to print ECG strip charts for the handoff between ACLS providers and hospital personnel. However, many AEDs that are designed for first responders do not include built-in printers. These types of portable AEDs are built for compactness and simplicity of use. Additionally, portable AEDs are typically used for emergency situations that occur infrequently, which is in contrast with paramedic defibrillators which are used on a regular basis. As a result, the expense of adding a built-in printer to a portable AED that is rarely used is not cost-effective. Nevertheless, it is desirable for an event summary to be recorded and made available for a second responder upon handoff of the patient.

More recent AED designs record the event summary information and store the resulting information digitally. The data is then transferred from the portable AED used by the first responder to the paramedic defibrillator. There are several mechanisms for transferring the data from one defibrillator to another. For example, the data can be stored to a removable storage medium in the form of a PCMCIA memory card. The information contained on the PCMCIA card is transferred by physically removing the PCMCIA card from the defibrillator and plugging it into another device which can up-load the information to the paramedic defibrillator. Manually transferring memory cards along with the patient during a handoff from the first responder to an ACLS provider, however, can be problematic where the memory cards are not compatible with the defibrillator belonging to the ACLS personnel or where the ACLS personnel does not have suitable equipment for transferring data from the memory card. There is also the disadvantage of increasing the cost of the AED by including a memory card.

The event summary information can also be transferred to the paramedic defibrillator using wired or wireless data transmission. Again, however, the format of the data, the software used for transferring the data, or the connectivity of the paramedic defibrillator may not be compatible with the first responder AED, preventing the transfer of event summary information during handoff.

Therefore, there is a need for a system and met hod for easily transferring medical information alongside the patient through the Chain of Survival.

In one aspect of the invention, a method and system for transferring medical information from a first cardiac monitoring device to a second cardiac monitoring device is provided. The method includes monitoring an ECG of a patient using the first cardiac monitoring device and generating output signals simulating the monitored ECG. The output signals are received as ECG signals at the second cardiac monitoring device.

In another aspect of the invention, a method and system for transferring medical information from a first medical monitoring device to a second device is provided. The method includes encoding the medical information from the first medical monitoring device as an ECG waveform and providing the ECG waveform having the encoded medical information to the second device as an input ECG waveform.

In another aspect of the invention, a defibrillator having electrodes, a controller and a connector is provided. The electrodes are configured to be attached to a patient and through which medical information of the patient is obtained. The controller is coupled to the electrodes and encodes the medical information for the patient as an ECG waveform. The connector is coupled to the controller and is configured to be coupled to ECG lead cables to provide the ECG waveform having the encoded medical information therethrough.

Certain details are set forth below to provide a sufficient understanding of the invention. However, it will be clear to one skilled in the art that the invention may be practiced without these particular details. Moreover, the particular embodiments of the present invention described herein are provided by way of example and should not be used to limit the scope of the invention to these particular embodiments. In other instances, well-known circuits, control signals, timing protocols, and software operations have not been shown in detail in order to avoid unnecessarily obscuring the invention.

The present invention addresses a problem common among first responders, emergency medical responders, emergency rooms and hospitals: how to transfer important patient information among medical instruments from different manufacturers and with no agreed-upon data transfer standards. The invention does this by taking advantage of a technology upon which agreement has been reached, ECG leads and the ECG acquisition systems of patient monitoring instruments. An implementation of the invention does this by transmitting patient event information in the form of a signal which can be received as a recognized ECG signal by other instruments. An implementation of the present invention may do this by means of standards cables which connect monitoring instruments to conventional ECG electrodes such as by snap connectors. The incompatibility of the data communication properties of various instruments is overcome by communicating previously recorded patient event information in a widely used ECG signal format.

Figure 1:
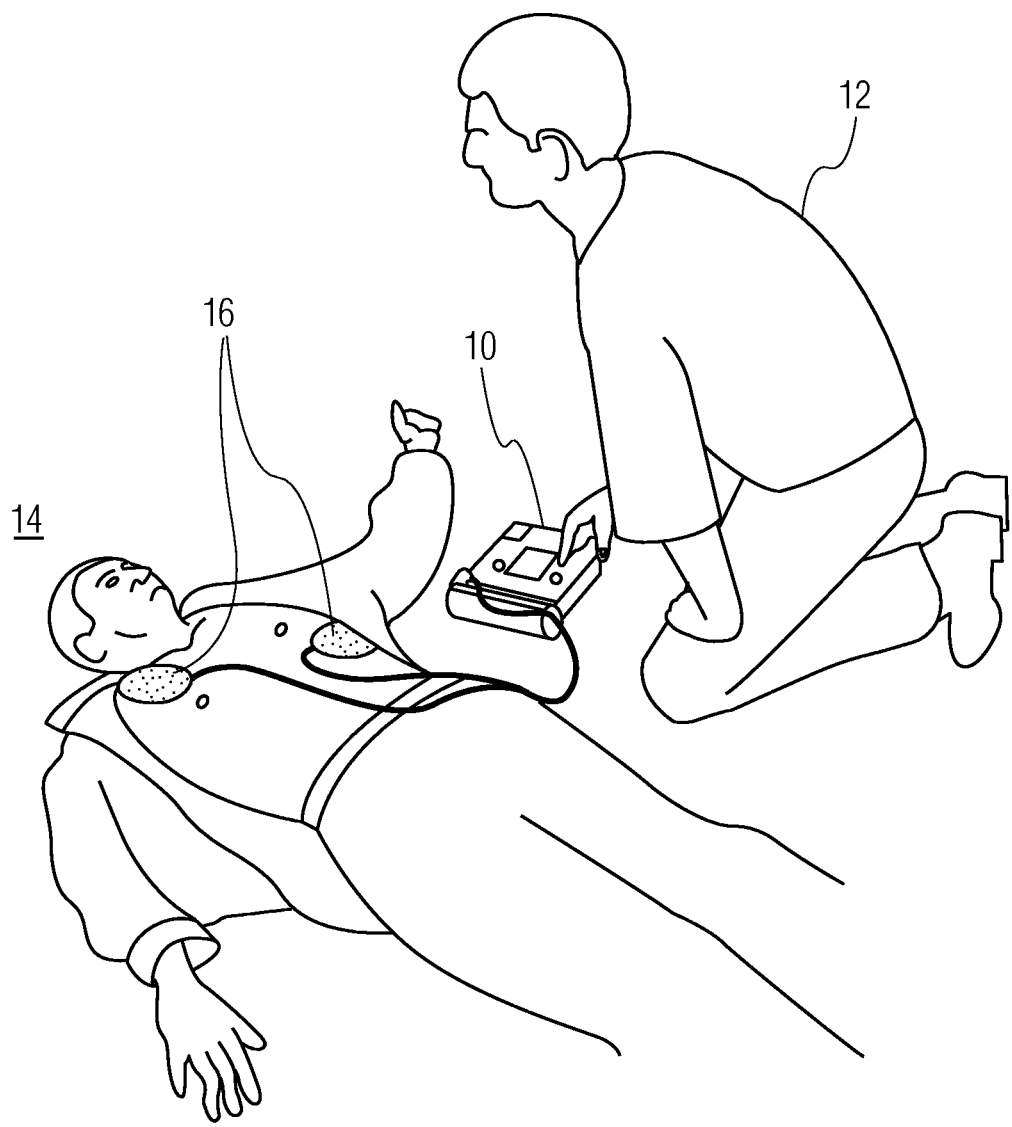
FIG. 1 is an illustration of a defibrillator being applied to a patient suffering from cardiac arrest.

FIG. 1 is an illustration of a defibrillator 10 being applied by a first responder 12 to resuscitate a patient 14 suffering from cardiac arrest. As previously discussed, in cardiac arrest the patient is stricken with a life threatening interruption to their normal heart rhythm, typically in the form of VF or VT that is not accompanied by a palpable pulse (shockable VT). In VF, the normal rhythmic ventricular contractions are replaced by rapid, irregular twitching that results in ineffective and severely reduced pumping by the heart. If normal rhythm is not restored quickly, a time frame commonly understood to be approximately 8 to 10 minutes, the patient will die. Conversely, the quicker defibrillation can be applied after the onset of VF, the better the chances that the patient will survive the event.

A pair of electrodes 16 are applied across the chest of the patient 14 by the first responder 12 in order to acquire an ECG signal from the patient's heart. The defibrillator 10, configured as an AED, then automatically analyzes the ECG signal to detect VF. If VF is detected, the defibrillator 10 signals the first responder 12 that a shock is advised. After detecting VF or other shockable rhythm, the first responder 12 then presses a button on the defibrillator 10 to deliver the shock to resuscitate the patient.

The information surrounding the event of resuscitation is important to providing proper emergency care of the patient 14 further along the Chain of Survival. As the patient 14 is handed off to ACLS providers or paramedics who provide more advanced treatment, critical medical information embodied as an event summary, explained in more detail below, travels with the patient 14.

Figure 2:
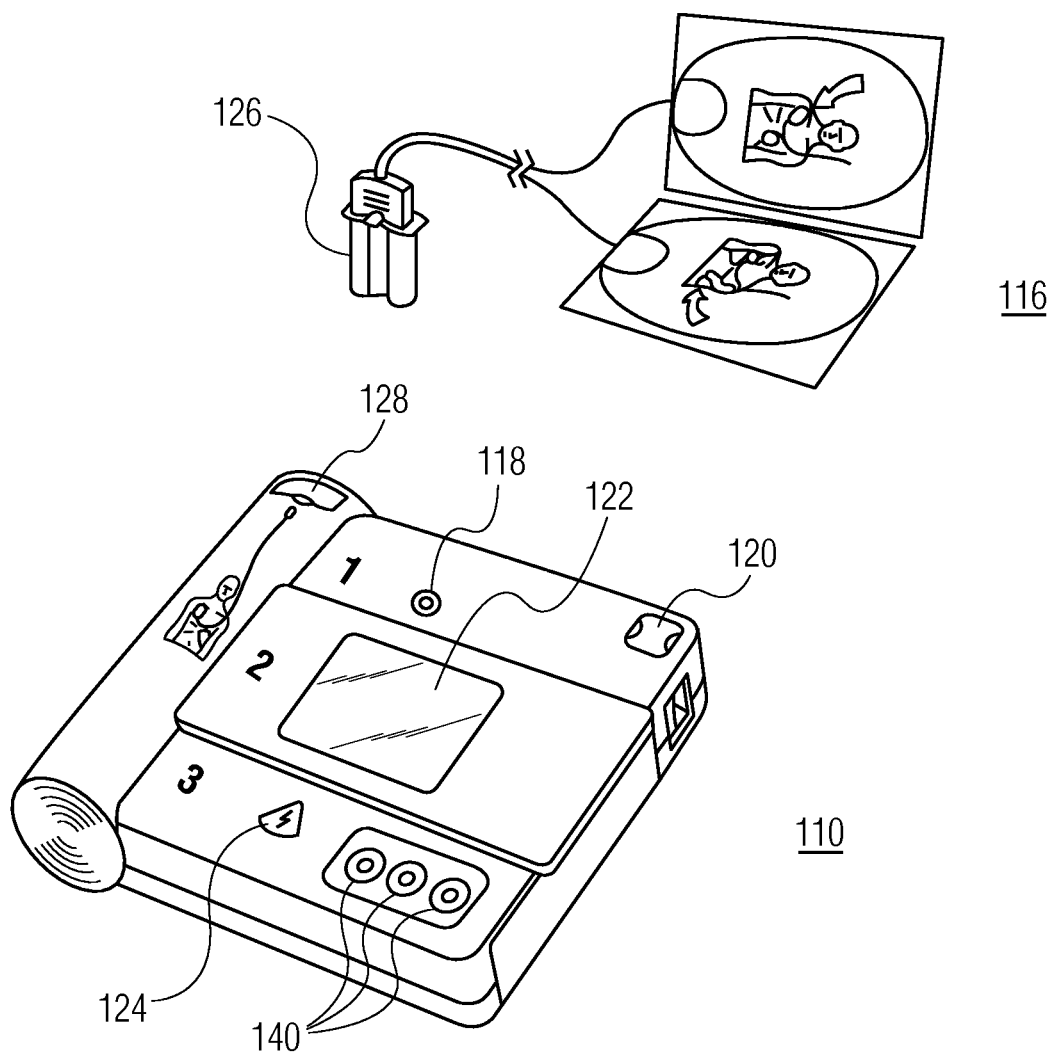
FIG. 2 is a more detailed illustration of a defibrillator and electrodes in accordance with an example of the present invention.

FIG. 2 illustrates defibrillator 110 according to an example of the present invention. Configured as an AED, the defibrillator 110 is designed for small physical size, light weight, and relatively simple user interface capable of being operated by personnel without high training levels or who otherwise would use the defibrillator 110 only infrequently. In contrast, a paramedic or clinical defibrillator, on the other hand, tends to be larger, heavier, and have a more complex user interface capable of supporting a larger number of manual monitoring and analysis functions. For purposes of the discussion that follows, the defibrillator 110 is used by the first responder 12 (FIG. 1) and a paramedic defibrillator is used by the ACLS provider.

A pair of electrodes 116 is connected to a connector 126 for insertion into a socket 128 on the defibrillator 110. On a top surface of the defibrillator 110 is located an on-off switch 118 which activates the defibrillator 110 and begins the process of prompting the first responder 12 to connect the electrodes 116 to the patient 14. A status indicator 120 provides a continual visual indication of the defibrillator status and the available battery charge. A display 122 preferably provides for display of text such as user prompts and graphics such as ECG waveforms. A shock button 124 provides for delivery of the shock to the patient 14 if ECG analysis indicates that a shockable rhythm is present. Administration of defibrillation shocks is done by prompting the user to manually press the shock button 124.

Connectors 140 are configured so that ECG lead cables of a paramedic or clinical defibrillator of an ACLS provider can be electrically connected to the defibrillator 110. As will be explained in more detail below, the defibrillator 110 compiles and stores an event summary during the treatment of the patient 14. During the handoff from the first responder 12 to the ACLS provider, portions of the event summary are recalled and transferred to the defibrillator of the ACLS provider through the ECG lead cables as an encoded ECG waveform. Event summary information is encoded in the encoded ECG waveform. An example of connectors 140 are snap connectors of the type that are used to couple ECG lead cables to disposable adhesive electrodes. Other connectors, however, can be used as well.

Figure 3:
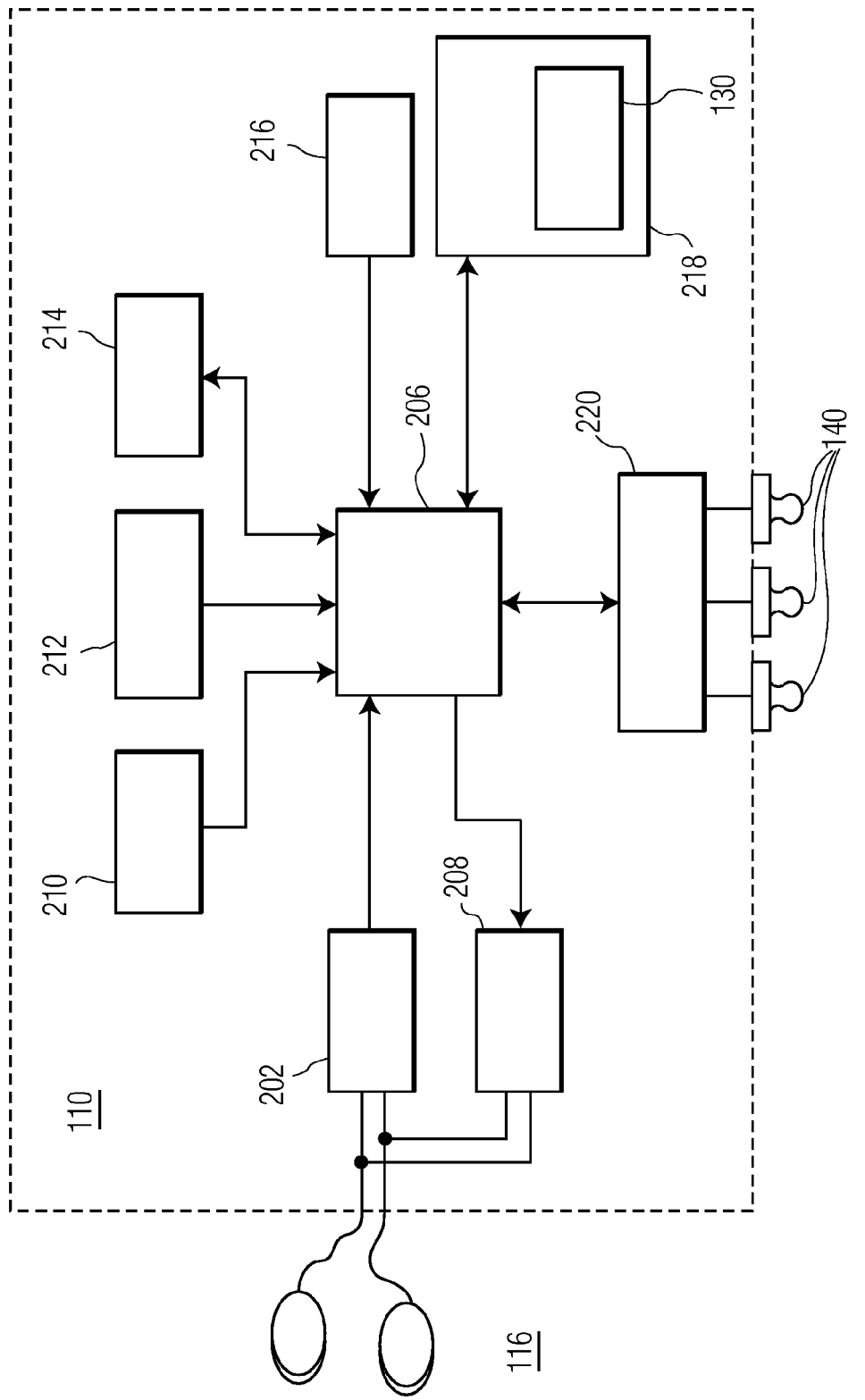
FIG. 3 is a simplified block diagram of the defibrillator of FIG. 2 in accordance with an example of the present invention.

FIG. 3 is a simplified block diagram of the defibrillator 110 (FIG. 2) according to an example of the present invention. The defibrillator 110 is shown for purposes of example as a simplified block diagram that could be used to implement an AED. An ECG front end 202 is connected to the pair of electrodes 116 that are connected across the chest of the patient 14. The ECG front end 202 operates to amplify, buffer, filter and digitize an electrical ECG signal generated by the patient's heart to produce a stream of digitized ECG samples. The digitized ECG samples are provided to a controller 206 that performs an analysis to detect VF, shockable VT or other shockable rhythm. If a shockable rhythm is detected, the controller 206 sends a signal to HV delivery 208 to charge up in preparation for delivering a shock. Pressing the shock button 124 then delivers a defibrillation shock from the HV delivery 208 to the patient 14 through the electrodes 116.

The controller 206 is coupled to receive inputs from an event mark 210. An event may be marked according to the time of event and type of event. The event mark 210 may be a button on the front panel that is pressed to mark selected events during the treatment of the patient 14, such as to mark drug delivery or the administration of CPR. The event mark 210 may also be automatically generated with annotations according to the occurrence of a predefined event, such as the pressing of the shock button 24 to record the time and energy level of the defibrillation shock. As many event markers as needed can be added to the event summary 130 to capture meaningful events and their respective times during the treatment of the patient 14.

The controller 206 is coupled to further receive input from a microphone 212 to produce a voice strip. The analog audio signal from the microphone 212 is preferably digitized to produce a stream of digitized audio samples which may be stored as part of an event summary 130 in a memory 218.

A user interface 214 may consist of the display 122, an audio speaker (not shown), and front panel buttons such as the on-off button 118 and shock button 124 for providing user control as well as visual and audible prompts. Additional buttons can be included on the front panel as well for use in navigating through menus and selecting defibrillator options. A clock 216 provides real-time or elapsed-time clock data to the controller 206 for time-stamping information contained in the event summary 130. The memory 218, implemented either as on-board RAM, a removable memory card, or a combination of different memory technologies, operates to store the event summary 130 digitally as it is compiled during treatment of the patient 14. The event summary 130 may include the streams of digitized ECG, audio samples, and other event data, as previously described.

During the handoff from the first responder 12 to the ACLS provider, at least a portion of the event summary 130 is recalled from memory 218 by the controller 206 and encoded in an encoded ECG waveform by an event summary encoder 220. The encoded ECG waveform can be applied to the connectors 140 so that a paramedic defibrillator coupled to the connectors 140 through ECG lead cables will receive the encoded ECG waveform. The ECG waveform encoded with the event summary 130 can be viewed by an ACLS provider who is trained to interpret the encoded ECG waveform to obtain event summary information. Additionally, a strip chart of the encoded waveform can be printed using a built-in printer of the paramedic defibrillator to produce a strip chart that can be transferred with the patient 14 at the next patient handoff.

Figure 4:
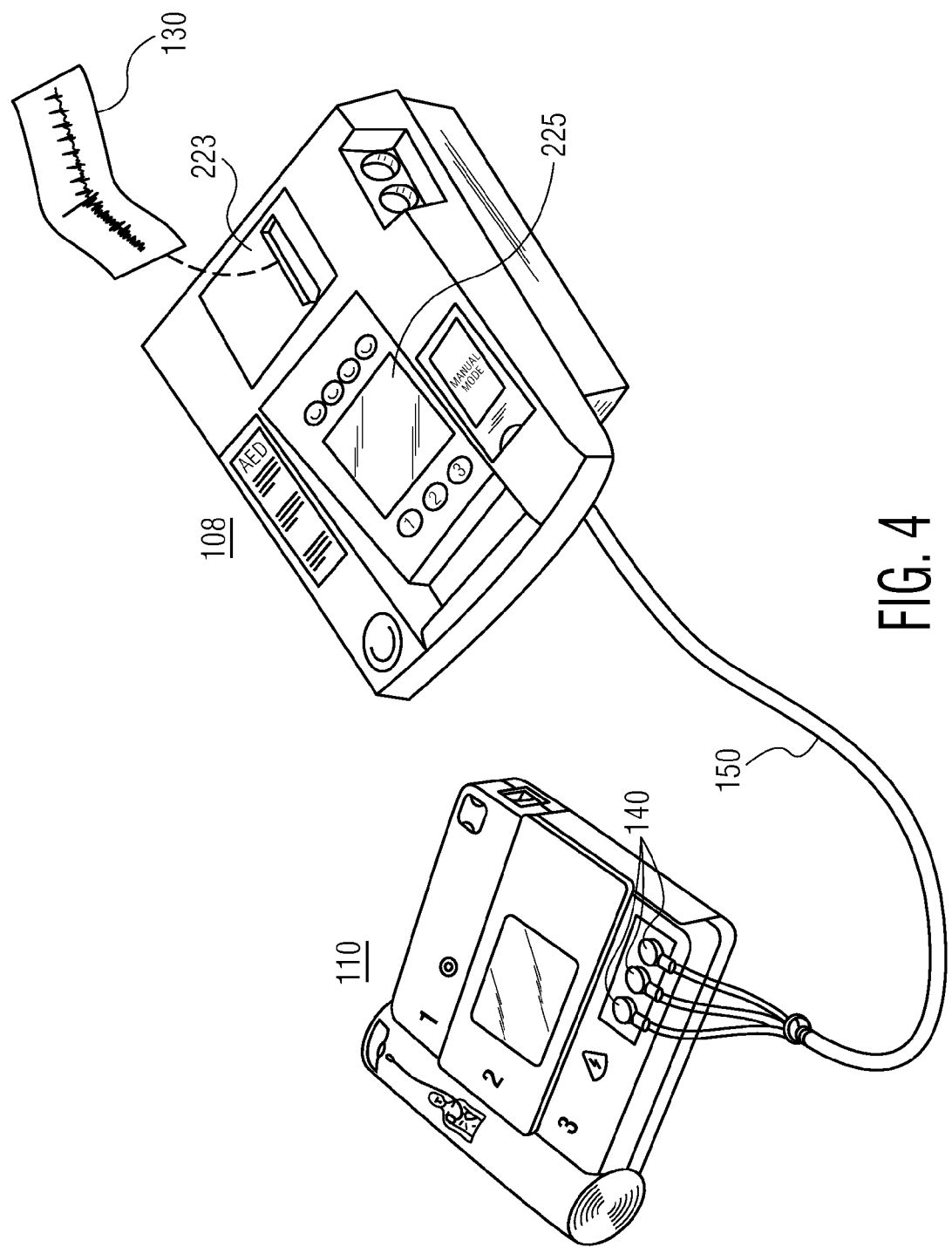
FIG. 4 is an illustration of the transfer of event summary information according to the present invention between the defibrillator of FIG. 2 and a paramedic defibrillator.

FIG. 4 is an illustration of the information transfer of the event summary 130 between the defibrillator 110 and a paramedic defibrillator 108 as may be done in the handoff of the patient 14 from the first responder 12 to the ACLS provider in accordance with an example of the present invention. A set of ECG lead cables 150 of the paramedic defibrillator 108 are connected to the defibrillator 110 via the connectors 140 to transfer the event summary 130 encoded in the form of an encoded ECG waveform. The ECG lead cables 150 are shown in FIG. 4 as having three leads. However, the illustration of FIG. 4 has been provided as an example, and the present invention includes alternative embodiments for accommodating ECG lead cables having greater or fewer leads.

The ACLS provider can view the encoded ECG waveform on a display 225 and print a strip chart having the encoded ECG waveform using a built-in printer 223 of the paramedic defibrillator 108. In this way, medical information collected by the defibrillator 110 that is important to the immediate treatment of the patient 14 may be transferred to the paramedic defibrillator 108, and then reviewed and put to use by the ACLS provider.

The transfer of event summary information 130 via encoded ECG waveform can be initiated through the use of the user interface 214 (FIG. 3). That is, buttons included on the front panel for navigating through menus and selecting defibrillator options can be used to manually enable a mode for transferring event summary information from the defibrillator 110. An automatic technique can be used as well, where connection of the ECG lead cables 150 to the connectors 140 are automatically detected by the controller 206 and, in response, an encoded ECG waveform is generated and provided to the paramedic defibrillator 108.

Different modes of transferring event summary information 130 can be included in the defibrillator 110. For example, in one mode, the encoded ECG waveform is used for transferring stored event summary information 130 that has been acquired and stored in the memory 218. In another mode, the encoded ECG waveform is used to transfer real-time event summary information, such as patient ECG signals. In this manner, the real-time information for the patient 14, who is still attached to the defibrillator 110, can be viewed and acquired by the paramedic defibrillator 108 without disturbing electrode connection with the patient 14. Another mode can be provided that allows for event summary information 130 to be replayed on the paramedic defibrillator 108 faster than real-time. In this mode, an ACLS provider can quickly scan the event summary information to review patient treatment prior to arriving on the scene, as well as identifying interesting sections in the encoded ECG waveform, such as a patient ECG signal included in the encoded ECG waveform, prior to selecting the section and printing a strip chart.

Figure 5:
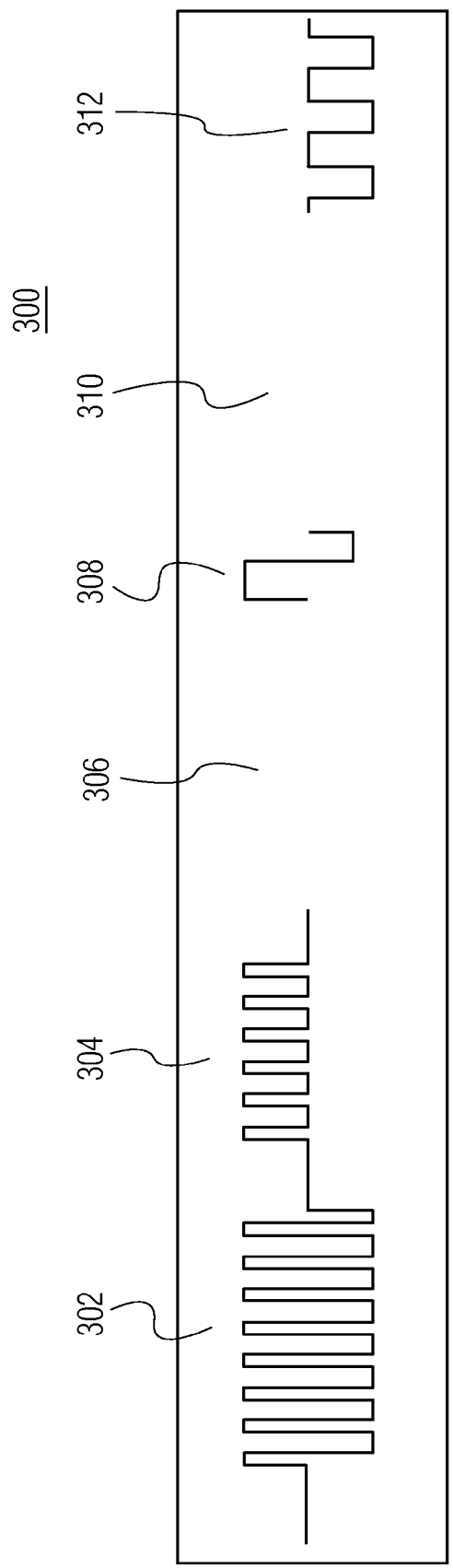
FIG. 5 is a diagram of event summary information encoded in an encoded ECG waveform according to an example of the present invention.

FIG. 5 illustrates event summary information 130 encoded in an ECG waveform provided by the defibrillator 110 to the paramedic defibrillator 108 and printed as an ECG strip chart 300 according to an embodiment of the present invention. The ECG strip chart 300 is a collection of digital samples taken from an analog ECG signal. The analog signal of the strip chart 300 provided to the paramedic defibrillator 108 is the encoded ECG waveform generate by the event summary encoder 220 in the defibrillator 110. The digital samples are reconstructed and displayed as vertical amplitude information ordered along a horizontal time axis to resemble the traditional paper ECG strip that is familiar to the physician.

The digital samples of the ECG signal must therefore be stored with both amplitude and time information in memory in the defibrillator 10.

Encoded in the encoded ECG waveform is event summary information, such as elapsed time since powering-on the AED, number of shocks delivered, peak current of the shocks delivered, and patient impedance. The resulting encoded ECG waveform can be interpreted by the ACLS provider to understand the treatment provided to the patient 14 up until the time of handoff. For example, as shown in FIG. 5, an elapsed time 302 from the moment when the defibrillator 110 is powered-on and when the event summary information 130 is transferred to the paramedic defibrillator 108 is used as a beginning marker for the encoded ECG waveform. The elapsed time 302 is encoded in the ECG waveform as an alternating signal at the beginning of the encoded ECG waveform. The alternating signal alternates between a positive peak value and a negative peak value, and the cycles of the alternating signal correspond to the number of minutes since powering-on the defibrillator 110. As shown in FIG. 5, eight minutes has elapsed between the time when the defibrillator 110 is initially switched on and when the event summary information 130 is transferred to the paramedic defibrillator 108. Alternatively, the elapsed time can be encoded by generating an alternating waveform having a length that corresponds to the elapsed time. For example, a relationship, such as 5 mm on the strip chart being equivalent to 1 minute of elapsed time, can be used to provide an indication of how much time has elapsed since the defibrillator 110 is powered-on. Thus, an alternating waveform at the beginning of the strip chart that alternates over a length of 40 mm can be interpreted as an elapsed time of 8 minutes.

Further encoded as a second marker in the encoded ECG waveform shown in the ECG strip chart 300 is the number of shocks 304 delivered to the patient 14 since the defibrillator 110 is powered-on and when the defibrillator 110 was connected to the paramedic defibrillator 108. A train of positive pulses is used to convey the number of shocks delivered, with each pulse corresponding to the delivery of one shock to the patient 14. In FIG. 5, the delivery of six shocks is encoded in the ECG waveform as a pulse train of six positive pulses. Alternatively, as previously described with respect to the elapsed time 302, the length of the train of positive pulses can be used to provide the number of shocks delivered to the patient 14. That is, a relationship, such as 5 mm on the strip chart being equivalent to one shock, can be used to provide an indication of the number of shocks delivered to the patient 14 prior to handoff to the ACLS provider.

The encoded ECG waveform provided by the defibrillator 110 further includes ECG signals 306, 310 of the patient 14. The patient ECG signals 306, 310 are obtained from the patient 14 by the defibrillator 110 during the treatment. Along with the patient ECG signals 306, 310 an event marker 308 is encoded into the ECG waveform to indicate when a shock is delivered and characteristics of the delivered shock. The event marker 308 shown in FIG. 5 indicates that a shock was delivered following acquisition of the patient ECG signal 306 and has an amplitude that is indicative of the peak current of the shock delivered to the patient 14, which as known, is related of patient impedance. In another embodiment, the amplitude of the event marker 308 can be interpreted to provide the patient impedance directly. The encoded ECG waveform is encoded with a end-of-field ("EOF") marker 312 that represents the end of the event summary information 130 encoded in the encoded ECG waveform and transferred to the paramedic defibrillator 108. The EOF marker is shown in the strip chart 300 as a negative pulse train that is output continuously.

Figure 6:
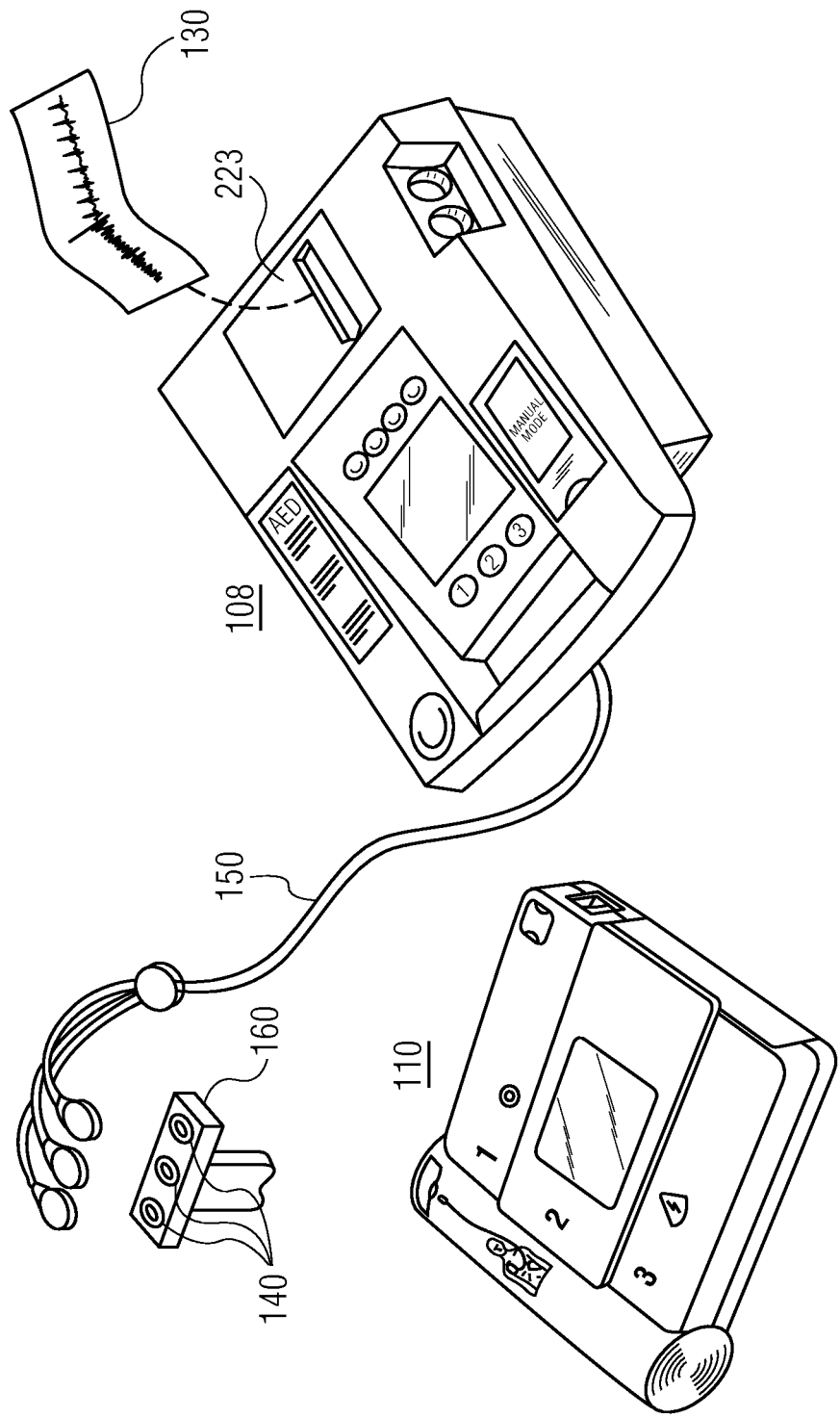
FIG. 6 is an illustration of the transfer of event summary information according to the present invention between a defibrillator and a paramedic defibrillator.

FIG. 6 is an illustration of the information transfer of the event summary 130 between the defibrillator 110 and a paramedic defibrillator 108 as may be done in the handoff of the patient 14 from the first responder 12 to the ACLS provider in accordance with another example of the present invention. An adapter 160 having connectors 140 is used to connect the paramedic defibrillator 108 to the defibrillator 110 through the ECG lead cables 150. The adapter 160 is inserted into the socket 128 on the defibrillator 110. In contrast to the information transfer illustrated in FIG. 4, the adapter 160 can be used to avoid including connectors 140 on the exterior of the defibrillator 110. Additionally, different adapters 160 can be used to provide connectivity to ECG lead cables 150 of various constructions, that is, having different connectors than "snap" connectors, or for use with ECG lead cables 150 having greater or fewer leads than the three shown in FIGS. 4 and 6. As will be appreciated, the electrical connection through the socket 128 can be modified to switch between use with the electrodes 116 and use with the adapter 160. Such modifications can be made using conventional designs, as well understood in the art.

From the foregoing it will be appreciated that, although specific embodiments of the invention have been described herein for purposes of illustration, various modifications may be made without deviating from the spirit and scope of the invention. For instance, the various examples described herein have been directed to transferring event summary information from a defibrillator configured as an AED to a paramedic defibrillator at handoff. However, some or all of the different aspects of the invention can be applied to transferring event summary information from one device to another device in the form of an encoded ECG waveform. One such alternative application is to couple a printer directly to the connectors of the defibrillator encoding event summary information for direct printing of the encoded ECG waveform. In another application, event summary information encoded in an ECG waveform could be used to transfer the information from a paramedic defibrillator to another defibrillator, such as at handoff from the ACLS provider to hospital personnel. An implementation of the present invention can also transmit pre-recorded patient information which is displayed in a visually distinctive manner compared to live patient information, so a caregiver is not misled to believe that the recorded information is the patients present physiological condition. It is also within the contemplation of the present invention to transmit the previously recorded patient data in a compressed format or at a rate which is greater than the real time display rate so that a large amount of patient information can be transferred to another instrument in a rapid and efficient manner. In many applications however a successor caregiver will only be interested in seeing the presenting rhythm seen by the defibrillator during the first twenty seconds after attachment of the first defibrillator to the patient. In such cases the information can be efficiently sent to the successor instrument at its original rate of receipt and be well within the reception capability of the typical ECG acquisition system. Accordingly, the invention is not limited except as by the appended claims.

What is claimed is:
1. A defibrillator, comprising:
electrodes configured to be attached to a patient through an electrode terminal and through which medical information of the patient is obtained;

a controller coupled to the electrodes and operable to encode the medical information of the patient as an ECG waveform; and a connector coupled to the controller and comprising an adapter configured to be coupled to the defibrillator through the electrode terminal, the adapter further comprising snap connectors configured to be coupled to ECG lead cables and provide the ECG waveform having the encoded medical information therethrough, wherein the medical information includes both of an ECG of the patient and an event summary information for the patient, the controller further operable to switch the electrode terminal between use with the electrodes for obtaining medical information and use with the adapter for providing the ECG waveform having the encoded medical information therethrough.

* * * * *